(12) United States Patent
Nishie et al.

(10) Patent No.: US 9,938,541 B2
(45) Date of Patent: Apr. 10, 2018

(54) AAV VARIANT

(71) Applicant: TAKARA BIO INC., Shiga (JP)

(72) Inventors: Toshikazu Nishie, Otsu (JP); Fuyuko Takashima, Kameoka (JP); Tatsuji Enoki, Kyotanabe (JP); Junichi Mineno, Uji (JP)

(73) Assignee: TAKARA BIO INC., Shigo (JP)

( * ) Notice: Subject to any disclaimer, the term of this patent is extended or adjusted under 35 U.S.C. 154(b) by 5 days.

(21) Appl. No.: 14/649,603

(22) PCT Filed: Dec. 20, 2013

(86) PCT No.: PCT/JP2013/084336
§ 371 (c)(1),
(2) Date: Jun. 4, 2015

(87) PCT Pub. No.: WO2014/103957
PCT Pub. Date: Jul. 3, 2014

(65) Prior Publication Data
US 2015/0315610 A1 Nov. 5, 2015

(30) Foreign Application Priority Data
Dec. 25, 2012 (JP) .................................. 2012-280485

(51) Int. Cl.
*C07H 21/04* (2006.01)
*C12N 15/86* (2006.01)
(Continued)

(52) U.S. Cl.
CPC ............ *C12N 15/86* (2013.01); *C07K 14/005* (2013.01); *C12N 7/00* (2013.01);
(Continued)

(58) Field of Classification Search
None
See application file for complete search history.

(56) References Cited

U.S. PATENT DOCUMENTS

| 8,927,514 B2 * | 1/2015 | Chatterjee ............ C07K 14/005 514/44 A |
| 2004/0002159 A1 * | 1/2004 | Xiao ...................... C12N 15/86 435/457 |

(Continued)

FOREIGN PATENT DOCUMENTS

| WO | WO 0113937 A1 * | 3/2001 | ......... C07K 14/4705 |
| WO | WO 0164835 A2 * | 9/2001 | ............. C07K 14/47 |
| WO | WO 2010093784 A2 * | 8/2010 | ........... C07K 14/005 |

OTHER PUBLICATIONS

International Search Report dated Feb. 25, 2014 in International Application No. PCT/JP2013/084336.
(Continued)

*Primary Examiner* — Janet L Andres
*Assistant Examiner* — M Franco G Salvoza
(74) *Attorney, Agent, or Firm* — Wenderoth, Lind & Ponack, L.L.P.

(57) ABSTRACT

The invention provides an AAV particle containing an adeno-associated viral (AAV) capsid protein having an amino acid sequence selected from the group consisting of SEQ ID NO: 15, SEQ ID NO: 16, SEQ ID NO: 24, and SEQ ID NO: 30 of the sequence listing; a nucleic acid that encodes this capsid protein; DNA containing this nucleic acid; a cell containing this DNA; and a method for producing this cell.

18 Claims, 1 Drawing Sheet

(51) Int. Cl.
C12N 15/00 (2006.01)
C12N 7/00 (2006.01)
C07K 14/005 (2006.01)

(52) U.S. Cl.
CPC ............ *C12N 2750/14122* (2013.01); *C12N 2750/14142* (2013.01); *C12N 2750/14143* (2013.01)

(56) References Cited

U.S. PATENT DOCUMENTS

2005/0106558 A1    5/2005   Perabo et al.
2005/0287122 A1*  12/2005   Bartlett .................... C12N 7/00
                                                    424/93.2

OTHER PUBLICATIONS

International Preliminary Report on Patentability dated Jun. 30, 2015 in International Application No. PCT/JP2013/084336.
Matthias Naumer et al., "Development and Validation of Novel AAV2 Random Libraries Displaying Peptides of Diverse Lengths and at Diverse Capsid Positions", Human Gene Therapy, May 2012, vol. 23, pp. 492-507.
Oliver J. Müller et al., "Random peptide libraries displayed on adeno-associated virus to select for targeted gene therapy vectors", Nature Biotechnology, Sep. 2003, vol. 21, No. 9, pp. 1040-1046.
Daniel A. Waterkamp et al., "Isolation of targeted AAV2 vectors from novel virus display libraries", The Journal of Gene Medicine, 2006, vol. 8, pp. 1307-1319.
Anne Girod et al., "Genetic capsid modifications allow efficient re-targeting of adeno-associated virus type 2", Nature Medicine, vol. 5, No. 9, Sep. 1999, pp. 1052-1056.
Mirta Grifman et al., "Incorporation of Tumor-Targeting Peptides into Recombinant Adeno-associated Virus Capsids", Molecular Therapy, vol. 3, No. 6, Jun. 2001, pp. 964-975.
Pei Wu et al., "Mutational Analysis of the Adeno-Associated Virus Type 2 (AAV2) Capsid Gene and Construction of AAV2 Vectors with Altered Tropism", Journal of Virology, Sep. 2000, vol. 74, No. 18, pp. 8635-8647.
Guangping Gao et al., "Clades of Adeno-Associated Viruses Are Widely Disseminated in Human Tissues", Journal of Virology, Jun. 2004, vol. 78, No. 12, pp. 6381-6388.
Kei Adachi et al., "A New Recombinant Adeno-Associated Virus (AAV)-Based Random Peptide Display Library System: Infection-Defective AAV1.9-3 as a Novel Detargeted Platform for Vector Evolution", Gene Ther Regul., Oct. 2010, vol. 5, pp. 31-55.
Chinese Office Action dated Jul. 5, 2016, issued in corresponding Chinese Patent Application No. 201380067755.7 (with English Translation).
Extended European Search Report dated Apr. 29, 2016, issued in corresponding European Patent Application No. 13867056.7.
Chinese Office Action dated Jan. 22, 2017 issued in corresponding Chinese Patent Application No. 201380067755.7 (with English translation).
Japanese Office Action dated Jul. 11, 2017 issued in corresponding Japanese Patent Application No. 2014-554421 (with Machine English Translation).
Office Action dated Aug. 14, 2017 issued in corresponding Chinese Patent Application No. 201380067755.7 with English translation.

* cited by examiner

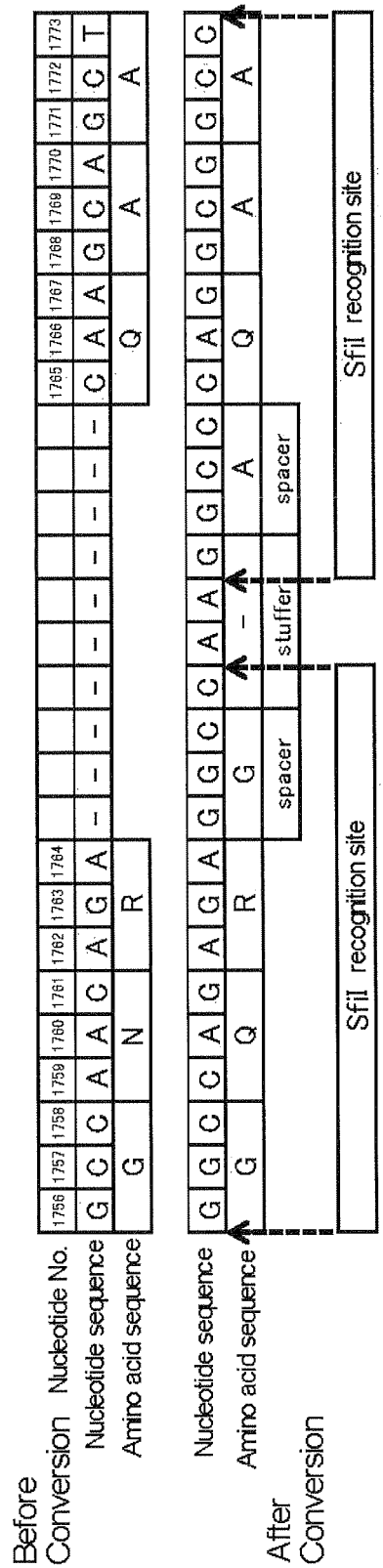

AAV VARIANT

TECHNICAL FIELD

The present invention relates to a nucleic acid encoding a variant of an adeno-associated virus (AAV) capsid protein, an AAV particle comprising the capsid protein variant, and a method of producing a gene-transduced cell by use of the particle.

BACKGROUND ART

AAV is a virus having a linear single-stranded DNA genome of 4.7 kb, comprising open reading frames of two genes rep and cap. The rep gene encodes four proteins necessary for genome replication (Rep78, Rep68, Rep52, and Rep40). The cap gene expresses three capsid proteins that assemble for formation of a viral capsid (VP1, VP2, VP3), and assembly-activating protein (AAP). Replication of AAV in nature relies on the presence of a helper virus such as an adenovirus or a herpes virus. In the absence of a helper virus, the genome of AAV is maintained in an episome or integrated into a chromosome of a host, so that the AAV is present in a latent state. Over one hundred serotypes and clades (non-patent literature 1) of AAV are currently identified. Particularly, development of vectors for gene delivery based on AAV2 is advanced.

In 1989, a gene delivery vector system based on AAV2 was developed for the first time. Vectors based on AAV have been found to have many advantages. Since wild-type AAV is nonpathogenic and has no etiological relation to any known diseases, vectors based on AAV are believed to be extremely safe. In addition, AAV has high gene transduction efficiency.

Administration of AAV particles enables long-period and stable gene transduction into various target organs and target cells. Until now, gene transduction with high efficiency into skeletal muscles, liver (hepatic cells), heart (cardiac muscle cells), nerve cells, pancreatic gland cells, and pancreatic islet cells has been reported. In addition, AAV has been used in human clinical trials. On the other hand, an attempt to change the cell tropism of AAV by alteration of capsid proteins of the AAV and an attempt to avoid removal of AAV particles by neutralizing antibodies have been made. For example, AAV capsids with tropism for specific organs and cells such as neuroglia cells, airway epithelial cells, coronary artery vascular endothelial cells, and lung, and AAV capsids with tropism for tumor cells such as glioblastoma cells, melanoma cells, lung cancer cells, and breast cancer cells have been created (non-patent literature 2).

CITATION LIST

Non-Patent Literatures

Non-patent literature 1: Gao et al., J. Virology, Vol. 78, pp. 6381-6388, 2004
Non-patent literature 2: Adachi K. et al., Genen Ther. Regul., Vol. 5, pp. 31-55, 2010

SUMMARY OF INVENTION

Problem to be Solved by the Invention

Objections of the present invention includes provision of an AAV capsid protein variant with tropism for heart and immune organs, in particular, lymph nodes, and provision of a method of efficiently introducing a gene into a lymph node.

Solutions to the Problems

The present inventors intensively made efforts to solve the above-described problems, and as a result, created an AAV particle comprising an AAV capsid protein having an amino acid sequence selected from the group consisting of SEQ ID NO: 15, SEQ ID NO: 16, SEQ ID NO: 24, and SEQ ID NO: 30 of the sequence listing. Thus the present invention was completed.

The present invention generally relates to:

[1] A nucleic acid encoding a variant of an adeno-associated virus (AAV) capsid protein which contains a peptide having an amino acid sequence selected from the group consisting of SEQ ID NO: 15, SEQ ID NO: 16, SEQ ID NO: 24, and SEQ ID NO: 30 of the sequence listing;
[2] The nucleic acid according to [1], wherein the AAV capsid protein is derived from AAV2;
[3] The nucleic acid according to [1], wherein the peptid is placed at a position following amino acid number 588 in VP1 of AAV2;
[4] A recombinant DNA comprising the nucleic acid according to any one of [1] to [3];
[5] A cell comprising the nucleic acid according to any one of [1] to [3] or the recombinant DNA according to [4];
[6] An AAV particle comprising a variant of an AAV capsid protein which contains a peptide having an amino acid sequence selected from the group consisting of SEQ ID NO: 15, SEQ ID NO: 16, SEQ ID NO: 24, and SEQ ID NO: 30 of the sequence listing;
[7] The AAV particle according to [6], wherein the AAV capsid protein is derived from AAV2;
[8] The AAV particle according to [6], wherein the peptide is placed at a position following amino acid number 588 in VP1 of AAV2;
[9] A method of producing a gene-transduced cell, the method comprising a step of bringing an AAV particle comprising a variant of an AAV capsid protein which contains a peptide having an amino acid sequence selected from the group consisting of SEQ ID NO: 15, SEQ ID NO: 16, SEQ ID NO: 24, and SEQ ID NO: 30 of the sequence listing into contact with a cell;
[10] The method according to [9], wherein the AAV capsid protein is derived from AAV2; and
[11] The method according to [9], wherein the peptide is placed at a position following amino acid number 588 in VP1 of AAV2.

Effects of the Invention

According to the present invention, a gene transduction system useful for gene transduction into heart and immune organs is provided. The AAV particle of the present invention has high cell tropism for immune organs, in particular, lymph nodes, and a gene transduced by the AAV particle can be strongly expressed.

BRIEF DESCRIPTION OF DRAWINGS

FIG. 1 shows a method of producing a nucleic acid construct enabling a capsid protein to contain a random peptide.

MODE FOR CARRYING OUT THE INVENTION

As used herein, the "adeno-associated virus" refers to a small virus belonging to the genus *Dependovirus* which lies within the family Parvoviridae and capable of infecting primates including human and the other mammals. Hereinafter, the adeno-associated virus is abbreviated as AAV. AAV has a non-enveloped shell (capsid) of a regular icosahedron and a linear single-stranded DNA inside the shell. As used herein, AAV includes the wild-type virus and derivatives thereof, and includes all serotypes and clades of AAV unless specified otherwise.

The "vector" as used herein means a molecule or an associated molecule that is used for mediating delivery of a polynucleotide to a cell and which comprises the polynucleotide or associates with the polynucleotide. Examples of the vector include vector DNAs such as plasmid vectors and phage vectors, viral vector particles, liposomes, and other vehicles for gene delivery, unless specified otherwise.

The "capsid protein" as used herein means a protein that is encoded by the cap gene present in the genome of AAV and constitutes the capsid of AAV. The wild-type AAV genome encodes three capsid proteins, and there are VP1, VP2 and VP3. As used herein, the capsid protein includes VP1, VP2 and VP3.

(1) Nucleic Acid Encoding an AAV Capsid Protein Variant

The nucleic acid of the present invention encodes a variant of an AAV capsid protein which contains a peptide having an amino acid sequence selected from the group consisting of SEQ ID NO: 15, SEQ ID NO: 16, SEQ ID NO: 24, and SEQ ID NO: 30 of the sequence listing.

The AAV capsid protein variant encoded by the nucleic acid of the present invention can be prepared by inserting the peptide into an AAV capsid protein of any AAV, such as AAV type 1 (AAV1), AAV type 2 (AAV2), AAV type 3 (AAV3), AAV type 4 (AAV4), AAV type 5 (AAV5), AAV type 6 (AAV6), AAV type 7 (AAV7), AAV type 8 (AAV8), AAV type 9 (AAV9), AAV type 10 (AAV10), AAV type 11 (AAV11), avian AAV, bovine AAV, canine AAV, equine AAV, or ovine AAV, or replacing a part of the amino acid sequence of the AAV capsid protein with the peptide (in other words, by making the AAV capsid protein contain the peptide). In the present invention, a capsid protein of AAV2 is preferably used.

For the nucleic acid of the present invention, the peptide which an AAV capsid protein is made to contain has an amino acid sequence selected from the group consisting of SEQ ID NO: 15, SEQ ID NO: 16, SEQ ID NO: 24, and SEQ ID NO: 30 of the sequence listing. In addition, a spacer sequence may be added to the N terminal and/or C terminal of the peptide. The spacer sequence preferably consists of 1 to 5 amino acid residues. The amino acid residues constituting the spacer sequence are particularly limited. For example, the spacer sequence may comprise an amino acid selected from the group consisting of glycine, alanine and serine.

As the AAV capsid protein that is made to contain the peptide, AAV VP1, VP2 or VP3 may be used. Only any one of VP1, VP2 and VP3 may be made to contain the peptide, or all of VP1, VP2 and VP3 may be made to contain the peptide. Furthermore, two capsid proteins such as VP1 and VP2, VP2 and VP3, or VP1 and VP3 may be made to contain the peptide. VP1 to VP3 are encoded by the cap gene region in the AAV genome. In one embodiment of the present invention, a region shared by VP1 to VP3 is made to contain the peptide so that a mutation can be introduced into all of VP1 to VP3. In another embodiment of the present invention, a gene encoding VP1, VP2 or VP3 is prepared separately from the cap gene region of AAV, and a mutation is introduced into the gene. In this case, a treatment that inhibits a capsid protein corresponding to the capsid protein encoded by the gene into which a mutation has been introduced from being expressed from the cap gene region of AAV may be performed.

In the case where AAV2 VP1 is used, the AAV capsid protein variant encoded by the nucleic acid of the present invention preferably contains the peptide at a position following amino acid number 588, that is, a position next to amino acid number 588. The amino acid number 588 of AAV2 VP1 corresponds to the amino acid number 451 of AAV2 VP2 and the amino acid number 386 of AAV2 VP3. A person skilled in the art can easily identify an amino acid of a capsid protein of AAV serotypes and clades other than AAV2 which corresponds to the amino acid at amino acid number 588 of AAV2 VP1. For example, see an alignment of amino acid sequences of VP1 shown in Gao et al., Proc. Natl. Acad. Sci. USA, Vol. 99, No. 18, pp. 11854-11859, 2002. For example, the amino acid number 588 of AAV2 VP1 corresponds to the amino acid number 589 of AAV1, the amino acid number 590 of AAV7, and the amino acid number 591 of AAV8.

The AAV capsid protein variant encoded by the nucleic acid of the present invention may be a wild-type AAV capsid protein altered to retain an amino acid sequence selected from the group consisting of SEQ ID NO: 15, SEQ ID NO: 16, SEQ ID NO: 24, and SEQ ID NO: 30 of the sequence listing and further comprise insertion, addition, substitution or deletion of one to several amino acids or more than one amino acid.

The nucleic acid of the present invention may be operably linked to a suitable control sequence. Examples of the control sequence include a promoter sequence, a polyadenylation signal, a transcription termination sequence, a upstream regulatory domain, a replication origin, an internal ribosomal entry site (IRES), and an enhancer. Examples of the promoter sequence include an inducible promoter sequence, and a constitutive promoter sequence. The control sequence may be an endogenous or exogenous sequence of AAV from which the capsid protein originates, a native sequence, or a synthesized sequence. The present invention also includes such a recombinant DNA capable of expressing the AAV capsid protein variant.

The recombinant DNA of the present invention is useful for delivering the nucleic acid of the present invention to cells in vitro, ex vivo or in vivo and imparting the ability to express the AAV capsid protein variant to the cells. Then, the cell to which the nucleic acid of the present invention is delivered is useful for producing AAV particles. The recombinant DNA can be particularly used for delivery or introduction of the nucleic acid of the present invention into animal cells, preferably mammal cells.

In the present invention, the recombinant DNA of the present invention can be prepared by making a DNA used as a vector retain the nucleic acid of the present invention. For example, a plasmid DNA, a phage DNA, a transposon, a cosmid DNA, an episomal DNA, or a viral genome can be used.

(2) Cell Containing the Nucleic Acid of the Present Invention

The present invention also provides a host cell, for example an isolated host cell, containing the nucleic acid of the present invention, specifically the recombinant DNA as described in above (1). An isolated cell is, for example, a cell line maintained in vitro. The host cell of the present invention is useful for production of the AAV particle of the present invention, as explained below. When the host cell of the present invention is used for producing AAV particles, the host cell may be referred to as a "packaging cell" or "producer cell". The host cell of the present invention may comprise the recombinant DNA of the present invention as described in above (1) integrated into the genome, or retain the recombinant DNA in the cell so as to transiently express the AAV capsid protein variant.

Introduction of the recombinant DNA of the present invention into a host cell can be performed by a known method. For example, electroporation, calcium phosphate precipitation, direct microinjection into cells, liposome-mediated gene transfection, or nucleic acid delivery using a high-speed particle gun can be used. When a viral vector is used, an infection method suitable for the vector may be selected. By use of such an established technique, the recombinant DNA of the present invention is introduced stably into a chromosome of a host cell or transiently into a cytoplasm of a host cell. For stable transformation, a selectable marker, for example a well-known selectable marker such as a neomycin resistance gene (encoding neomycin phosphotransferase), or a hygromycin B resistance gene (encoding aminoglycoside phosphotransferase (APH)) can be linked to the recombinant DNA of the present invention.

As the host cell, various cells, for example, mammal cells including mouse cells and primate cells (for example, human cells) or insect cells can be used. Examples of suitable mammal cells include, but not limited to, primary cells and cell lines. Examples of suitable cell lines include 293 cells, COS cells, HeLa cells, Vero cells, 3T3 mouse fibroblasts, C3H10T1/2 fibroblasts, CHO cells, and cells derived from them.

(3) AAV Particle Comprising an AAV Capsid Protein Containing an Amino Acid Sequence Encoded by the Nucleic Acid of the Present Invention The AAV particle of the present invention is an AAV particle comprising an AAV capsid protein variant containing a peptide having an amino acid sequence selected from the group consisting of SEQ ID NO: 15, SEQ ID NO: 16, SEQ ID NO: 24, and SEQ ID NO: 30 of the sequence listing. The AAV particle can be produced from the host cell described in above (2). The AAV particle of the present invention has tropism for heart (cardiac muscle cells) and immune organs (immune cells), in particular lymph nodes, and is useful for gene introduction into para-aortic lymph nodes and/or femoral lymph nodes. The gene introduced by the AAV particle of the present invention is strongly expressed in the above-mentioned tissues, organs and cells.

For production of the AAV particle, a cell comprising some elements necessary for production of AAV particles can be used as a packaging cell. The first element is a vector genome (also referred to as an expression vector) for a recombinant AAV which may be replicated in a host cell and packaged in an AAV particle. The recombinant AAV vector genome comprises a heterologous polynucleotide of interest, and AAV inverted terminal repeat (ITR) sequences located on each side, i.e. 5'- and 3'-sides of the heterologous polynucleotide of interest. The heterologous polynucleotide of interest may have a control sequence for the expression. The nucleotide sequences of ITR sequences are known. For AAV2-ITR sequences, for example, see Human Gene Therapy, Vol. 5, pp. 793-801, 1994. As the AAV ITR sequences, ITR sequences derived from any of various AAV serotypes including AAV1, AAV2, AAV3, AAV4, AAV5, AAV7, and etc. can be used. The ITR sequences used in the present invention may be derived from a wild-type AAV or may be altered by insertion, deletion or substitution of a nucleotide(s). The ITR sequences enable replication of the recombinant AAV vector genome in the presence of Rep protein, and enable incorporation of the recombinant AAV vector genome into a capsid particle in the formation of an AAV particle.

The size of the heterologous polynucleotide of interest which can be harbored inside the AAV particle of the present invention is generally less than about 5 kilo bases (kb). The heterologous polynucleotide of interest may be, for example, a gene encoding a protein of interest which a recipient lacks or loses, a gene encoding a protein having a desired biological or therapeutic activity (for example, antimicrobial, antiviral, or antitumor activity), a desired nucleotide sequence encoding RNA that inhibits or decreases production of a harmful or undesired protein, or a nucleotide sequence encoding an antigenic protein. The heterologous polynucleotide of interest can be appropriately selected according to purposes.

In one embodiment of the present invention, the recombinant AAV vector genome lacks the cap gene region and/or the rep gene region. In this embodiment, an AAV particle into which the recombinant AAV vector genome is packaged is not replicated alone to form an AAV particle again in an infected cell.

The second element necessary for production of AAV particles is a construct that provides AAV helper functions. The construct encodes AAV-derived genes providing AAV gene products required for formation of AAV particles. In other words, the construct comprises one or both of the major AAV ORFs, coding regions of the rep gene region and cap gene region. For production of the AAV particle of the present invention, at least a nucleic acid encoding an AAV capsid protein variant containing a peptide having an amino acid sequence selected from the group consisting of SEQ ID NO: 15, SEQ ID NO: 16, SEQ ID NO: 24, and SEQ ID NO: 30 of the sequence listing is used as the cap gene. The host cell of the present invention described in above (2) which is capable of expressing the variant can be used for production of the AAV particle. The AAV particle has a shell composed of many capsid proteins. All of the capsid proteins may be variants, or a part of the capsid proteins may be variants and the others may be wild-type capsid proteins. The AAV particle of the present invention may comprise one kind of a variant of a capsid protein or plural kinds of variants of a capsid protein.

The rep gene of AAV is contained in coding regions of the rep gene, and includes genes encoding replication proteins Rep78, Rep68, Rep52 and Rep40. These Rep expression products are shown to possess many functions, including recognition, binding and nicking of the AAV genomic DNA replication origin, DNA helicase activity, and modulation of transcription from AAV-derived promoters.

The third element necessary for production of AAV particles is helper virus functions (also referred to as accessary functions) for AAV replication. For introduction of helper functions, an adenovirus is generally used. However, other viruses such as herpes simplex virus type-1 or type-2, and vaccinia virus can be also used. When a virus is used, a host cell is infected with the virus as a helper virus. For example, since expression of adenovirus early genes is only required for packaging of AAV particles, an adenovirus that does not reveal expression of late genes may be used. An adenovirus variant lacking late gene expression (for example, ts100K or ts149 adenovirus variant) can be also used. A nucleic acid construct that provides helper virus functions can be also prepared by use of nucleic acids necessary for helper virus functions isolated from a helper virus, and then can be introduced into a host cell. The construct that provides helper virus functions comprises a nucleotide sequence providing one or plural helper virus functions, and is provided to a host cell in the form of a plasmid, phage, transposon, cosmid, or other viruses.

For production of AAV particles, (a) a step of introducing the first element, the recombinant AAV vector genome into a host cell, (b) a step of introducing the second element, the construct that provides AAV helper functions into the host cell, and (c) a step of introducing the third element, the helper virus functions into the host cell are performed. The order of steps (a) to (c) may be any order. When the first to third elements are introduced into a host cell, the rep gene-expression products excise and replicate the recombinant vector genome. The capsid proteins expressed form a capsid, and the recombinant vector genome is packaged in the capsid to produce an AAV particle. When the host cell expresses an AAV capsid protein variant, the shell of the AAV particle produced comprises the AAV capsid protein variant.

The AAV particle can be isolated and purified from a culture supernatant or a lysate of the host cell by various purification methods such as CaCl density-gradient centrifugation. When a virus is used in above-described step (c), for example, a step of separating the AAV particle from the helper virus on the basis of their size may be added. The AAV particle can be also separated from the helper virus on the basis of a difference in affinity for heparin. Furthermore, the remaining helper viruses can be inactivated by known methods. For example, adenoviruses can be inactivated by heating at about 60° C., for example, for 20 minutes or more. Since AAV particles are very stable to heat, the above-described treatment is effective for selective removal of adenoviruses used as the helper virus.

(4) Method of Producing a Gene-transduced Cell of the Present Invention

The AAV particle of the present invention obtained by above (3) is used for delivery of a heterologous polynucleotide of interest to a cell for the purpose of gene therapy or other purposes. The AAV particle is generally introduced into a cell in vivo or in vitro. For in vitro introduction, the AAV particle is brought into contact with a cell obtained from a living body. Then, the cell can be also transplanted into a living body. For introduction of the cell into a living body, the cell can be formulated as a pharmaceutical composition, and various techniques such as intramuscular, intravenous, subcutaneous and intraperitoneal administration can be used. For in vivo transduction, the AAV particle is formulated as a pharmaceutical composition, and in general, administered parenterally (for example, administered via a intramuscular, subcutaneous, intratumor, transdermal, or intraspinal route). The pharmaceutical composition comprising the AAV particle contains a pharmaceutically acceptable carrier and, as necessary, other agent, drug, stabilizer, carrier, adjuvant, diluent, and the like.

EXAMPLES

Preparation Example 1

Construction of pAAV-AsRed2

A pAsRed2-C1 vector (manufactured by Clontech Laboratories, Inc.) as a template was subjected to PCR, to obtain an about 1.6 kb fragment in which a recognition site of restriction enzyme NotI was added upstream of a CMV promoter and downstream of a polyA signal. This PCR product was digested with NotI (manufactured by TAKARA BIO Inc.) to obtain an insert DNA. A pAAV-MCS expression vector (manufactured by CELL BIOLABS, Inc.) was digested with NotI to prepare an about 2.9 kb fragment. This fragment was used as a vector. Into this vector, the insert DNA was ligated using DNA ligation kit <Mighty Mix> (manufactured by TAKARA BIO Inc.). *E. coli* HST08 premium competent cells (manufactured by TAKARA BIO Inc.) were transformed with the vector. From clones thus obtained, plasmid DNAs were extracted, and a plasmid DNA into which CMV promoter-AsRed2-MCS-polyA signal were inserted in this order was named pAAV-AsRed2.

Example 1

Preparation of AAV2 Random Peptide Plasmid Library

Plasmid vector pAV1 (ATCC Number: 37215) carrying the genome of AAV2 was extracted from distribution host *Escherichia coli* HB101. From the extracted plasmid, a genomic DNA of AAV2 (about 4.7 kb) was excised with restriction enzyme BglII (manufactured by TAKARA BIO Inc.). This genomic DNA was inserted into pUC118 BamHI/BAP (manufactured by TAKARA BIO Inc.). The plasmid thus obtained DNA was named AAV2WG/pUC118.

The AAV2WG/pUC118 was digested with restriction enzyme ScaI (manufactured by TAKARA BIO Inc.) to obtain an about 0.8 kb fragment containing nucleotides 1190 to 2017 of the cap gene. This fragment was inserted into pUC118 HincII/BAP (manufactured by TAKARA BIO Inc.). The plasmid DNA thus obtained was named Cap-ScaI/pUC118. Then, the Cap-ScaI/pUC118 was subjected to PCR so as to perform a series of alterations in which nucleotide sequence AAC(N) consisting of nucleotides 1759 to 1761 of the Cap gene in the Cap-ScaI/pUC118 was converted to CAG(Q), 10 nucleotides consisting of GGC as a spacer, CAAG as a stuffer, and GCC as a spacer were inserted between nucleotide 1764 and nucleotide 1765, and nucleotide sequence CAA(Q) GCA(A) GCT(A) consisting of nucleotides 1765 to 1773 was converted to CAG(Q) GCG (A) GCC(A), wherein the letters in brackets show the encoded amino acids. Thus, two recognition sites of restriction enzyme SfiI and the spacer, stuffer and spacer between the SfiI recognition sites were inserted. FIG. 1 shows nucleotides sequence before and after the conversion of nucleotides 1756 to 1773 of the Cap gene. The nucleotide sequence before the conversion is shown by SEQ ID NO: 1 of the sequence listing. The nucleotide sequence after the conversion is shown by SEQ ID NO: 2 of the sequence listing. The plasmid DNA comprising the converted nucleotide sequence was named Cap-ScaI-S4/pUC118. For infusion cloning, the Cap gene portion in the Cap-ScaI-S4/pUC118 was amplified by PCR to obtain an about 0.8 kb fragment. This fragment was used as an insert DNA.

The AAV2WG/pUC118 was subjected to PCR so that a mutation was introduced into a recognition site of restriction enzyme ScaI in an ampicillin resistant gene and a recognition site of restriction enzyme SfiI in the Rep gene, so that these recognition sites were converted to sequences that were not recognized by the restriction enzymes. For the ScaI recognition site, nucleotide sequence GAG(E) consisting of nucleotides 304 to 306 of the ampicillin resistant gene was converted to GAA(E). The sequence before the conversion is shown by SEQ ID NO: 3 and the sequence after the conversion is shown by SEQ ID NO: 4. For the SfiI recognition site, nucleotide sequence GCC(A) consisting of nucleotides 217 to 219 of the Rep gene was converted to GCA(A). The sequence before the conversion is shown by SEQ ID NO: 5 and the sequence after the conversion is shown by SEQ ID NO: 6. The plasmid DNA thus obtained was digested with ScaI (manufactured by TAKARA BIO Inc.) to obtain a linear vector lacking about 0.8 kb that was a part of the Cap gene. This was used as a linear vector for in-fusion cloning.

Using In-Fusion (registered trademark) HD cloning kit (manufactured by Clontech Laboratories, Inc.) and a cloning enhancer (manufactured by Clontech Laboratories, Inc.), the insert DNA was inserted into the linear vector, and thereby directional cloning was performed. The plasmid DNA thus obtained was named AAV2WG-Cap-ScaI-S4/pUC118Sx.

An oligo DNA (SEQ ID NO: 7) comprising a nucleotide sequence encoding a random peptide of 7 amino acids was generated by artificial synthesis. A double stranded DNA was prepared from the oligo DNA by reaction with a primer (SEQ ID NO: 8) and a klenow fragment (manufactured by TAKARA BIO Inc.) at 37° C. for 3 hours. The double stranded DNA was purified using a Nucleotide removal kit (manufactured by QIAGEN) and then digested with restriction enzyme BglI (manufactured by TAKARA BIO Inc.). This DNA was inserted into AAV2WG-Cap-ScaI-S4/pUC118Sx digested with SfiI, using DNA ligation kit <Mighty Mix> (manufactured by TAKARA BIO Inc.). The plasmid thus obtained was named AAV2WG-RPL/pUC118Sx, and used as an AAV2 random peptide plasmid library.

Example 2

Preparation of AAV2 Random Peptide Virus Library (1) Seeding of AAV293 Cell

Cultured AAV293 cells (manufactured by Stratagene Corp.) were collected, and then suspended in DMEM (manufactured by Sigma) containing 10% FBS and 2 mM sodium L-glutamate at $5 \times 10^4$ cells/mL. Into a T225 cm² flask for cell culture (manufactured by Corning Incorporated), 40 mL of the suspension containing AAV293 cells was put and then cultured at 37° C. for 72 hours in a $CO_2$ incubator.

(2) Introduction of Plasmid into AAV293 Cell

The AAV293 cells were transfected with 400 ng of AAV2WG-RPL/pUC118Sx obtained in Example 1 and 40 μg of pHELP (manufactured by CELL BIOLABS, Inc.) by a general calcium phosphate method. Six hours after the transfection, the medium was completely removed. After 40 mL of DMEM containing 2% FBS and 2 mM sodium L-glutamate was added, the cells were cultured at 37° C. for 48 hours in a $CO_2$ incubator.

(3) Collection of AAV2 Random Peptide Virus Library

Into the T225 cm² flask being incubated, 0.5 mL of 0.5 M EDTA was added, followed by standing for several minutes. Then, the AAV293 cells were exfoliated and collected into a 50 mL tube by pipetting, and centrifuged at 300×g for 10 minutes. Then, a supernatant was removed. The cells were resuspended in 2 mL TBS (Tris-buffered saline) per flask, and then subjected thrice to sequential treatments consisting of freezing with ethanol/dry ice for 15 minutes, thawing in a 37° C. water bath, and vortex for 1 minute, to collect a cell lysate containing an AAV-random peptide virus library. To the cell lysate, 5 μL of 1 M $MgCl_2$ per 1 mL of TBS and Benzonase (registered trademark) nuclease (manufactured by Merck KGaA) at a final concentration of 200 U/mL were added, followed by reaction at 37° C. for 30 minutes. Then, the reaction was terminated by an addition of 6.5 μL of 0.5 M EDTA per 1 mL of TBS. The cell lysate was centrifuged at 10000 rpm and 4° C. for 10 minutes, and then a supernatant was collected as an AAV vector solution.

(4) Titer Quantitation of AAV Vector Solution by Real-time PCR

Into 2 μL of the AAV vector solution, 2 μL of 10× DNaseI buffer, 15.2 μL of water for injection (manufactured by Otsuka Pharmaceutical Co., Ltd.) and 0.8 μL of DNaseI (manufactured by TAKARA BIO Inc.) were added, and the mixture was incubated at 37° C. for 1 hour to remove free genomic DNAs and plasmid DNAs. For inactivation of DNaseI, the mixture was heated at 99° C. for 10 minutes. Then, 15 μL of water for injection, 4 μL of 10×ProK buffer [0.1 M Tris-HCl (pH 7.8), 0.1 M EDTA, 5% SDS] and 1 μL of ProK (manufactured by TAKARA BIO Inc.) were added, and the mixture was incubated at 55° C. for an hour. Then, for inactivation of ProK, the mixture was heated at 95° C. for 10 minutes. This sample was subjected to AAV titer quantitation using SYBR (registered trademark) Premix ExTaq2 (manufactured by TAKARA BIO Inc.) and primers (SEQ ID NO: 9 and SEQ ID NO: 10) according to instructions attached to a kit. The sample was diluted 50-fold with water for injection, and 2 μL of the diluted solution was used for titer quantitation. As a standard, a linear DNA obtained by restriction enzyme digestion of pAV1 was used.

Example 3

Purification of AAV Random Peptide Virus Library (1) Purification 1 by Cesium Chloride Density-gradient Centrifugation In a 40 PA tube for ultracentrifugation (manufactured by HITACHI-KOKI Co., Ltd.), 4 mL of a cesium chloride solution adjusted to a density of 1.5, 4 mL of a cesium chloride solution adjusted to a density of 1.25, and 28 mL of the AAV vector solution prepared in Example 2-(4) were layered in this order from the bottom. The tube was centrifuged at 25000 rpm and 16° C. for 3 hours by ultracentrifuge HIMAC (manufactured by HITACHI-KOKI Co., Ltd.). After centrifugation, 28 mL of the solution was removed from the top of the tube, and then, an aliquot of 0.7 mL of the solution was subsequently collected from the top into a 1.5 mL tube. In the same manner as Example 2-(4), titer of the AAV vector contained in each collected solution was quantitated.

(2) Purification 2 by Cesium Chloride Density-gradient Centrifugation

In several fractions that were shown to have high titer in Example 3-(1), a cesium chloride solution adjusted to a density of 1.39 was added to reach a total volume of 10.5 mL. The solution thus obtained was put in a 13 PA tube for ultracentrifugation (manufactured by HITACHI-KOKI Co., Ltd.), and then centrifuged at 38000 rpm and 18° C. for 16 hours. After centrifugation, an aliquot of 0.7 mL of the solution was successively collected from the top of the tube. In the same manner as Example 2-(4), titer of the AAV vector contained in each collected solution was quantitated.

(3) Dialysis by Desalting

Several fractions that were shown to have high titer in Example 3-(2) were mixed and then added to a Slide-Alyzer dialysis cassette (manufactured by Pierce). The purified AAV solution was desalted by dialysis with 1 L of phosphate buffered saline (PBS) at 4° C. for 3 hours twice and dialysis with 500 mL of a PBS/5% sorbitol solution at 4° C. overnight. Then, the solution was collected, sterilized with a 0.22 μm filter (manufactured by Millipore), and stored at −80° C. until just before use. Separately, titer of the purified AAV solution was quantitated in the same manner as Example 2-(4).

Example 4

Screening of AAV2 Random Peptide Library (1) Tail Vein Administration to Mouse

The purified AAV solution obtained in Example 3-(3) was administered to BALB/c mice via a tail vein at 1×10$^{13}$ viral genome (VG)/kg. After 72 hours from the administration, inguinal lymph nodes and para-aortic lymph nodes were collected, and a genomic DNA was extracted by use of NucleoSpin (registered trademark) tissue (manufacture by MACHEREY-NAGEL GmbH & Co. KG) (Round 1).

(2) Recloning of Random Peptide Sequence by PCR

A DNA encoding the random peptide sequence was amplified using the genomic DNA extracted in Example 4-(1) was used as a template, and PrimeSTAR (registered trademark) GXL DNA polymerase (manufactured by TAKARA BIO Inc.). As primers, forward primer 1 (SEQ ID NO: 11) and reverse primer 1 (SEQ ID NO: 12) were used. PCR was performed by repeated 30 cycles and each cycle of PCR consisted of 98° C. for 10 seconds, 55° C. for 15 seconds, and 68° C. for 40 seconds. Then, a twenty-fifth part of the PCR reaction solution, forward primer 2 (SEQ ID NO: 13) and reverse primer 2 (SEQ ID NO: 14) were used to prepare a reaction mixture in the same amount as before. The reaction mixture was subjected to PCR with 30 cycles, in which each cycle consisted of 98° C. for 10 seconds, 55° C. for 15 seconds, and 68° C. for 15 seconds. From the reaction solution thus obtained, a DNA was purified by use of Nucleospin extract II (manufacture by MACHEREY-NAGEL GmbH & Co. KG), and digested with restriction enzyme BglI. After electrophoresis, a digested product was purified by use of Nucleospin extract II (manufacture by MACHEREY-NAGEL GmbH & Co. KG), and recloned into AAV2WG-Cap-ScaI-S4/pUC118Sx as prepared in Example 1 by use of DNA ligation kit <Mighty Mix> (manufactured by TAKARA BIO Inc.).

(3) Production and Purification of AAV2 Random Peptide Virus Library

Production and purification of an AAV2 random peptide virus library were performed using the plasmid obtained in Example 4-(2) by the same methods as those described in Example 2 and Example 3.

(4) Screening

In the same manner as Example 4-(1), screening was performed and a genomic DNA was extracted (Round 2). Furthermore, using the extracted genomic DNA, recloning, production and purification of a library, and screening were performed again, and a genomic DNA was extracted (Round 3).

(5) Sequencing of Random Peptide

At each screening stage (Round 1 to Round 3), ninety and several clones were subjected to sequencing of the AAV random peptide plasmid library. Peptide sequences that appeared in the clones more than once and the appearance frequency are shown in Table 1 for the clones collected from para-aortic lymph nodes and Table 2 for the clones collected from femoral lymph nodes.

TABLE 1

| Sequence | SEQ ID NO | Round 1 | Round 2 | Round 3 |
|---|---|---|---|---|
| VEEGRRGQ | 15 | 1 | 55 | 87 |
| GGDATRG | 16 | — | 2 | 6 |
| GGGRVAE | 17 | — | 3 | 1 |
| DWGGAWE | 18 | — | 5 | — |
| GQAGGAA | 19 | 3 | 4 | — |
| GGWGGSA | 20 | — | 3 | — |
| GPVNGGG | 21 | — | 2 | — |
| AGGGLGG | 22 | — | 2 | — |
| ARGGGW | 23 | — | 2 | — |
| GAMGGSV | 24 | — | 2 | — |
| AVLCGAA | 25 | 3 | — | — |
| GERTSGP | 26 | 2 | — | — |
| GSGGAED | 27 | 2 | — | — |
| GVARGAA | 28 | 2 | — | — |
| VGGSLVS | 29 | 2 | — | — |
| Total | | 94 | 94 | 96 |

TABLE 2

| Sequence | SEQ ID NO | Round 1 | Round 2 | Round 3 |
|---|---|---|---|---|
| GDDGTRG | 30 | — | 83 | 94 |
| VEEGRRGQ | 31 | — | 1 | — |
| VASVWRE | 32 | 2 | 1 | — |
| GTASSGG | 33 | 2 | 1 | — |
| GAMGGSV | 34 | — | 1 | — |
| ASAGGYQ | 35 | 2 | — | — |
| GASGLVA | 36 | 2 | — | — |
| GTASSGG | 37 | 2 | — | — |
| Total | | 95 | 95 | 95 |

As shown in Table 1 and Table 2, the specific peptides accumulated in the target tissues. In particular, VEEGRRGQ (SEQ ID NO: 15) and GGDATRG (SEQ ID NO: 16) tended to accumulate in para-aortic lymph nodes, and GDDGTRG (SEQ ID NO: 30) tended to accumulate in femoral lymph nodes. In both para-aortic and femoral lymph nodes, accumulation of GAMGGSV (SEQ ID NOs: 24 and 34) was found. Thus, it is suggested that these peptide sequences tend to infect lymph nodes.

Example 5

Evaluation of Tropism of AAV Vector having Acquired Peptide Sequence (1) Construction of pRC-GDDGTRG The AAV2WG-Cap-ScaI-S4/pUC118Sx clone having sequence GDDGTRG as obtained in Example 4-(5) was digested with restriction enzymes SnaBI (manufactured by TAKARA BIO Inc.) and HindIII (manufactured by TAKARA BIO Inc.) to obtain a fragment. The fragment was ligated to a vector fragment obtained by digestion of a pAAVRC2 vector (manufactured by CELL BIOLABS, Inc.) with SnaBI and HindIII by DNA ligation kit <Mighty Mix> (manufactured by TAKARA BIO Inc.) to obtain helper plasmid pRC-GDDGTRG.

(2) Production and Purification of AAV2-AsRed2 Capsid Variant

AAV293 cells seeded on T255 cm$^2$ were transfected with 25 μg of the pAAV-AsRed2 prepared in Preparation Example 1, 25 μg of pHELP, and 25 μg of the pRC-GDDGTRG prepared in Example 5-(1) by a general calcium phosphate method. As a control, transfection with a pAAVRC2 vector carrying the wild-type capsid instead of the pRC-GDDGTRG was performed. Six hours after the transfection, the medium was completely removed, 40 mL of DMEM containing 2% FBS and 2 mM sodium L-glutamate was added to the cells, and the cells were cultured at 37° C. for 48 hours in a $CO_2$ incubator. Then, two different AAV-AsRed2 vectors were produced and purified by the methods described in Example 2-(3) and Example 3. Then, titer of the AAV vectors was quantitated by the method described in Example 2-(4).

(3) Administration of AAV Purified Solution to Mouse

The purified AAV solution obtained in Example 5-(2) was administered to mice via a tail vein at $1×10^{13}$ VG/kg per mouse.

(4) Preparation of Genomic DNA from Lymph Node and other Tissue and Quantitation of AAV Genome The mice to which AAV was administered in Example 5-(3) were euthanized a week or 6 weeks after administration, and each tissue was collected. A genomic DNA was extracted from each tissue by use of NucleoSpin tissue (manufactured by MACHEREY-NAGEL GmbH & Co. KG). The extracted genomic DNA as a sample was subjected to real-time PCR to determine the amount of the AAV vector genome contained in each tissue. Table 3 shows the number of AAV genomic DNA molecules per 1 µg of the total genomic DNA in each tissue.

TABLE 3

|  | After 1 week | | After 6 weeks | |
| --- | --- | --- | --- | --- |
|  | Wild-type | GDDGTRG | wild-type | GDDGTRG |
| Liver | 1.37.E+05 | 7.75.E+03 | 7.25.E+04 | 4.95.E+03 |
| Lung | 9.68.E+03 | 1.08.E+05 | 7.22.E+03 | 2.36.E+03 |
| Heart | 1.23.E+04 | 1.07.E+04 | 1.69.E+03 | 1.61.E+03 |
| Kidney | 1.47.E+04 | 7.79.E+03 | 5.24.E+03 | 4.32.E+03 |
| Spleen | 7.15.E+05 | 5.57.E+05 | 7.35.E+04 | 3.69.E+03 |
| Femoral LN | 2.05.E+05 | 1.94.E+05 | 1.71.E+04 | 2.20.E+05 |
| Para-aortic LN | 3.70.E+04 | 2.66.E+05 | 4.37.E+04 | 2.34.E+04 |
| Axillary LN | 8.37.E+04 | 1.83.E+05 | 1.38.E+04 | 9.13.E+04 |

(LN: Lymph node)
Viral genome/µg of DNA

As can be seen from Table 3, the AAV vector comprising the capsid having sequence GDDGTRG tended to transfer into lymph nodes, and the AAV genome was maintained even 6 weeks after administration.

(5) Extraction of RNA from Lymph Node and other Tissue and Quantitation of AsRed2 Expression Each tissue obtained in Example 5-(4) was reacted at 4° C. in RNAlater (manufactured by QIAGEN) overnight. Then, the tissue was homogenated with BioMasher II (manufactured by Nippi, Inc.), and an RNA was extracted by use of Nucleospin RNA II (manufacture by MACHEREY-NAGEL GmbH & Co. KG). By use of Onestep SYBR PrimeScript RT-PCR kit (manufactured by TAKARA BIO Inc.), the expression of the AsRed2 gene (primers having sequences of SEQ ID NOs: 38 and 39) and the expression of a mouse GAPDH gene (primers having sequences of SEQ ID NOs: 40 and 41) for correction were quantitated. The AsRed2 expression amounts corrected based on the GAPDH expression amounts are shown in Table 4.

TABLE 4

|  | After 1 week | | After 6 weeks | |
| --- | --- | --- | --- | --- |
|  | Wild-type | GDDGTRG | wild-type | GDDGTRG |
| Liver | 6.2 | 3.7 | 0.89 | 0.23 |
| Lung | 0.2 | 1.2 | 0.03 | 0.14 |

TABLE 4-continued

|  | After 1 week | | After 6 weeks | |
| --- | --- | --- | --- | --- |
|  | Wild-type | GDDGTRG | wild-type | GDDGTRG |
| Heart | 0.0 | 21.0 | 0.03 | 63.81 |
| Kidney | 0.0 | 0.0 | 0.00 | 0.02 |
| Spleen | 0.0 | 3.4 | 0.04 | 0.00 |
| Femoral LN | 0.0 | 5.5 | 0.03 | 4.59 |
| Para-aortic LN | −3.9 | 23.6 | −0.16 | 20.82 |
| Axillary LN | 0.1 | 12.4 | 0.10 | 3.68 |

As can be seen from the above results, when the AAV vector comprising the capsid variant into which sequence GDDGTRG was inserted was used, high expression efficiencies were found in various lymph nodes and heart as compared with the AAV vector comprising the wild-type capsid.

Example 6

Evaluation of Anti-tumor Activity by IL-12 Gene-carrying AAV2 Variant (1) Construction of pAAV2-IL12

A mouse IL-12a-p35 gene (GenBank Accession No.: NM_008351) was amplified by use of a mIL12a-fwd primer (SEQ ID NO: 42) and a mIL12a-rev primer (SEQ ID NO: 43), a cDNA prepared from a mouse spleen as a template, and PrimeSTAR MAX DNA Polymerase (manufactured by TAKARA BIO Inc.). The amplified fragment thus obtained was ligated to a vector fragment obtained by digestion of a pAAV-MCS expression vector (manufactured by CELL BIOLABS, Inc.) with EcoRI (manufactured by TAKARA BIO Inc.) and BamHI (manufactured by TAKARA BIO Inc.) by use of an In-Fusion HD cloning kit (manufactured by Clontech Laboratories, Inc.) to obtain pAAV2-mIL12a. Then, a mouse IL-12b-p40 gene (GenBank Accession No.: NM_008352) was amplified by use of a mIL12b-fwd primer (SEQ ID NO: 44) and a mIL12b-rev primer (SEQ ID NO: 45) wherein a T2A sequence was incorporated into the primers, a cDNA prepared from a mouse spleen as a template, and PrimeSTAR MAX DNA Polymerase (manufactured by TAKARA BIO Inc.). The amplified fragment thus obtained was ligated to a vector fragment obtained by digestion of the pAAV2-mIL12a with BamHI and HindIII by use of an In-Fusion HD cloning kit (manufactured by Clontech Laboratories, Inc.) to obtain pAAV2-mIL12. In other words, the pAAV2-mIL12 retains a polynucleotide in which the IL-12a-p35 gene, T2A, and IL-12b-p40 gene are ligated in this order, and produces mature IL12 protein.

(2) Production and Purification of AAV2-IL12 Viral Vector

AAV293 cells seeded on T255 $cm^2$ were transfected with 25 µg of the pAAV2-mIL12 prepared in Example 6-(1), 25 µg of pHELP, and 25 µg of the pRC-GDDGTRG prepared in Example 5-(1) by a general calcium phosphate method. As a control, transfection with a pAAV-AsRed2 instead of the pAAV2-mIL12 was performed. Six hours after the transfection, the medium was completely removed, 20 mL of DMEM containing 2% FBS and 2 mM sodium L-glutamate was added to the cells, and the cells were cultured at 37° C. for 48 hours in a $CO_2$ incubator. Then, AAV vectors were produced and purified by the methods described in Example 2-(3) and Example 3. Then, titer of the AAV vectors was quantitated by the method described in Example 2-(4).

(3) Tail Vein Administration of Purified AAV Solution and Subcutaneous Administration of CT26 Tumor Cell to Mouse The purified AAV solution was administered to mice via a tail vein at $5 \times 10^{13}$ VG/kg per mouse. Two weeks after administration, a CT26 tumor cell line was subcutaneously administered to the back of the mice at $1 \times 10^6$ cells per mouse. Then, the tumor size was successively quantitated. The average tumor size at each measurement date is shown in Table 5.

TABLE 5

| | Average tumor size after administration of tumor ($mm^3 \pm $ S.E.M.) | |
|---|---|---|
| Days | Control (n = 4) | AAV2-IL12 (n = 6) |
| 10 | 34.3 ± 1.6 | 4.6 ± 5.0 |
| 14 | 66.8 ± 3.7 | 20.2 ± 11.8 |
| 18 | 139.7 ± 40.1 | 37.1 ± 20.7 |
| 25 | 400.1 ± 167.0 | 202.2 ± 108.8 |
| 31 | 1183.9 ± 314.8 | 499.3 ± 314.0 |

As shown in Table 5, the AAV2-IL12 comprising the GDDGTRG capsid variant had anti-tumor activity.

Example 7

Evaluation-2 of Tropism of AAV Vector having Acquired Peptide Sequence (1) Construction of pRC-GGDATRG and pRC-GAMGGSV From the AAV2WG-Cap-ScaI-S4/pUC118Sx clone having sequence GGDATRG (SEQ ID NO: 16) or GAMGGSV (SEQ ID NO: 24) as obtained in Example 4-(5), helper plasmid pRC-GGDATRG and pRC-GAMGGSV were obtained in the same manner as Example 5-(1).

(2) Production and Purification of AAV2-AsRed2 Capsid Variant

The pRC-GGDATRG and pRC-GAMGGSV prepared in Example 7-(1) were used to produce and purify an AAV-AsRed2 vector having each capsid variant by the method described in Example 5-(2). Then, titer of the AAV vectors was quantitated by the method described in Example 2-(4).

(3) Administration of Purified AAV Solution to Mouse

The purified AAV solution was administered to mice via a tail vein at $1 \times 10^{11}$ VG/kg per mouse. Separately, the AAV vector having the wild-type or the GDDGTRG variant prepared in Example 5-(2) was administered to mice.

(4) Extraction of RNA from Lymph Node and other Tissue and Quantitation of AsRed2 Expression The mice to which AAV was administered in Example 7-(3) were euthanized 6 weeks after administration, and each tissue was collected. Each tissue was reacted at 4° C. in RNAlater (manufactured by QIAGEN) overnight. Then, an RNA was prepared in the same manner as Example 5-(5). By use of Onestep SYBR PrimeScript PLUS RT-PCR kit (manufactured by TAKARA BIO Inc.), the expression of the AsRed2 gene (primers having sequences of SEQ ID NOs: 38 and 39) and the expression of a mouse GAPDH gene (primers having sequences of SEQ ID NOs: 40 and 41) for correction were quantitated. The AsRed2 expression amounts corrected based on the GAPDH expression amounts are shown in Table 6.

TABLE 6

| | Wild-type | GDDGTRG | GGDATRG | GAMGGSV |
|---|---|---|---|---|
| Liver | 2.23 | 0.55 | 0.22 | 1.11 |
| Lung | 0.11 | 0.24 | 0.06 | 0.07 |
| Heart | 0.17 | 99.38 | 36.57 | 39.36 |
| Kidney | 0.13 | 0.08 | 0.10 | 0.18 |
| Spleen | 1.54 | 0.76 | 0.73 | 0.39 |
| Femoral LN | 0.14 | 11.15 | 3.22 | 3.99 |
| Para-aortic LN | 0 | 6.53 | 1.60 | 3.15 |
| Axillary LN | 2.53 | 9.50 | 7.32 | 4.16 |

As can be seen from the above results, even when the AAV vector comprising the GGDATRG or GAMGGSV capsid variant was used, high expression efficiencies were found in various lymph nodes and heart as compared with the AAV vector comprising the wild-type capsid.

In addition, as can be seen from the above results, the peptide sequences that appeared more than once when ninety and several clones at each screening stage (Round 1 to Round 3) were subjected to sequencing of the plasmid library had high tropism for lymph nodes and heart.

INDUSTRIAL APPLICABILITY

According to the present invention, a capsid protein variant having tropism for heart and immune organs, in particular lymph nodes is provided, and a method of efficiently introducing a gene into lymph nodes is provided.

SEQUENCE LISTING FREE TEXT

SEQ ID NO:1: AAV2 capsid 586-591 coding sequence
SEQ ID NO:2: Converted AAV2 capsid coding sequence
SEQ ID NO:3: Ampicillin resistance gene before conversion
SEQ ID NO:4: Ampicillin resistance gene after conversion
SEQ ID NO:5: AAV2 rep gene before conversion
SEQ ID NO:6: AAV2 rep gene after conversion
SEQ ID NO:7: DNA sequence coding random peptide
SEQ ID NO:8: Primer for synthesizing double strand DNA
SEQ ID NO:9: Forward primer for quantitation of AAV titer
SEQ ID NO:10: Reverse primer for quantitation of AAV titer
SEQ ID NO:11: Forward primer1 for amplification of random peptide coding region
SEQ ID NO:12: Reverse primer1 for amplification of random peptide coding region
SEQ ID NO:13: Forward primer2 for amplification of random peptide coding region
SEQ ID NO:14: Reverse primer2 for amplification of random peptide coding region
SEQ ID NO:15: Peptide sequence comprised AAV capsid protein mutant
SEQ ID NO:16: Peptide sequence comprised AAV capsid protein mutant
SEQ ID NO:17: Peptide sequence comprised AAV capsid protein mutant
SEQ ID NO:18: Peptide sequence comprised AAV capsid protein mutant
SEQ ID NO:19: Peptide sequence comprised AAV capsid protein mutant
SEQ ID NO:20: Peptide sequence comprised AAV capsid protein mutant
SEQ ID NO:21: Peptide sequence comprised AAV capsid protein mutant
SEQ ID NO:22: Peptide sequence comprised AAV capsid protein mutant
SEQ ID NO:23: Peptide sequence comprised AAV capsid protein mutant SEQ ID NO:24: Peptide sequence comprised AAV capsid protein mutant
SEQ ID NO:25: Peptide sequence comprised AAV capsid protein mutant
SEQ ID NO:26: Peptide sequence comprised AAV capsid protein mutant
SEQ ID NO:27: Peptide sequence comprised AAV capsid protein mutant
SEQ ID NO:28: Peptide sequence comprised AAV capsid protein mutant
SEQ ID NO:29: Peptide sequence comprised AAV capsid protein mutant
SEQ ID NO:30: Peptide sequence comprised AAV capsid protein mutant
SEQ ID NO:31: Peptide sequence comprised AAV capsid protein mutant
SEQ ID NO:32: Peptide sequence comprised AAV capsid protein mutant
SEQ ID NO:33: Peptide sequence comprised AAV capsid protein mutant
SEQ ID NO:34: Peptide sequence comprised AAV capsid protein mutant
SEQ ID NO:35: Peptide sequence comprised AAV capsid protein mutant
SEQ ID NO:36: Peptide sequence comprised AAV capsid protein mutant
SEQ ID NO:37: Peptide sequence comprised AAV capsid protein mutant
SEQ ID NO:38: Forward primer for amplification of AsRed2
SEQ ID NO:39: Reverse primer for amplification of AsRed2
SEQ ID NO:40: Forward primer for amplification of mouse GAPDH
SEQ ID NO:41: Reverse primer for amplification of mouse GAPDH
SEQ ID NO:42: mIL12a-fwd primer
SEQ ID NO:43: mIL12a-rev primer
SEQ ID NO:44: mIL12b-fwd primer
SEQ ID NO:45: mIL12b-rev primer

The invention claimed is:

1. A nucleic acid encoding a variant of one or more adeno-associated virus (AAV) capsid proteins selected from the group consisting of VP1, VP2 and VP3 which contains a spacer sequence and a peptide consisting of an amino acid sequence selected from the group consisting of SEQ ID NO: 15, SEQ ID NO: 16, SEQ ID NO: 24, and SEQ ID NO: 30, and wherein the AAV capsid protein containing the peptide has tropism for heart and/or immune organs.

2. The nucleic acid according to claim 1, wherein the AAV capsid protein is derived from AAV2.

3. The nucleic acid according to claim 1, wherein the peptide is placed at a position following amino acid number 588 in VP1, a position following amino acid number 451 in VP2 or a position following amino acid number 386 in VP3.

4. A recombinant DNA comprising the nucleic acid according to claim 1.

5. An isolated host cell comprising the nucleic acid according to claim 1.

6. An AAV particle comprising a variant of one or more AAV capsid proteins selected from the group consisting of VP1, VP2 and VP3 which contains a spacer sequence and a peptide consisting of an amino acid sequence selected from the group consisting of SEQ ID NO: 15, SEQ ID NO: 16, SEQ ID NO: 24, and SEQ ID NO: 30.

7. The AAV particle according to claim 6, wherein the AAV capsid protein is derived from AAV2.

8. The AAV particle according to claim 7, wherein the peptide is placed at a position following amino acid number 588 in VP1, a position following amino acid number 451 in VP2 or a position following amino acid number 386 in VP3.

9. A method of producing a gene-transduced cell, the method comprising a step of bringing an AAV particle comprising a variant of one or more AAV capsid proteins selected from the group consisting of VP1, VP2 and VP3 which contains a spacer sequence and a peptide consisting of an amino acid sequence selected from the group consisting of SEQ ID NO: 15, SEQ ID NO: 16, SEQ ID NO: 24, and SEQ ID NO: 30 into contact with a cell.

10. The method according to claim 9, wherein the AAV capsid protein is derived from AAV2.

11. The method according to claim 9, wherein the peptide is placed at a position following amino acid number 588 in VP1, a position following amino acid number 451 in VP2 or a position following amino acid number 386 in VP3.

12. A recombinant DNA comprising the nucleic acid according to claim 2.

13. A recombinant DNA comprising the nucleic acid according to claim 3.

14. An isolated host cell comprising the nucleic acid according to claim 2.

15. An isolated host cell comprising the nucleic acid according to claim 3.

16. An isolated host cell comprising the recombinant DNA according to claim 4.

17. The nucleic acid according to claim 1, wherein the spacer sequence consists of 1 to 5 amino acid residues.

18. The nucleic acid according to claim 1, wherein the spacer sequence comprises an amino acid selected from the group consisting of glycine, alanine and serine.

* * * * *

SEQUENCE LISTING

```
<160> NUMBER OF SEQ ID NOS: 47

<210> SEQ ID NO 1
<211> LENGTH: 18
<212> TYPE: DNA
<213> ORGANISM: Artificial Sequence
<220> FEATURE:
<223> OTHER INFORMATION: AAV2 capsid 586-591 coding sequence

<400> SEQUENCE: 1
gccaacagac aagcagct                                                     18

<210> SEQ ID NO 2
<211> LENGTH: 28
<212> TYPE: DNA
<213> ORGANISM: Artificial Sequence
<220> FEATURE:
<223> OTHER INFORMATION: Converted AAV2 capsid coding sequence

<400> SEQUENCE: 2
ggccagagag gccaaggccc aggcggcc                                          28

<210> SEQ ID NO 3
<211> LENGTH: 45
<212> TYPE: DNA
<213> ORGANISM: Artificial Sequence
<220> FEATURE:
<223> OTHER INFORMATION: Ampicillin resistance gene before conversion

<400> SEQUENCE: 3
tattctcaga atgacttggt tgagtactca ccagtcacag aaaag                       45

<210> SEQ ID NO 4
<211> LENGTH: 45
<212> TYPE: DNA
<213> ORGANISM: Artificial Sequence
<220> FEATURE:
<223> OTHER INFORMATION: Ampicillin resistance gene after conversion

<400> SEQUENCE: 4
tattctcaga atgacttggt tgaatactca ccagtcacag aaaag                       45

<210> SEQ ID NO 5
<211> LENGTH: 45
```

```
<212> TYPE: DNA
<213> ORGANISM: Artificial Sequence
<220> FEATURE:
<223> OTHER INFORMATION: AAV2 rep gene before conversion

<400> SEQUENCE: 5
gaatggcgcc gtgtgagtaa ggccccggag gccctttct ttgtg                45

<210> SEQ ID NO 6
<211> LENGTH: 45
<212> TYPE: DNA
<213> ORGANISM: Artificial Sequence
<220> FEATURE:
<223> OTHER INFORMATION: AAV2 rep gene after conversion

<400> SEQUENCE: 6
gaatggcgcc gtgtgagtaa ggcaccggag gccctttct ttgtg                45

<210> SEQ ID NO 7
<211> LENGTH: 56
<212> TYPE: DNA
<213> ORGANISM: Artificial Sequence
<220> FEATURE:
<223> OTHER INFORMATION: DNA sequence coding random peptide
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t

<400> SEQUENCE: 7
cagtcggcca gagaggcnnk nnknnknnkn nknnknnkgc ccaggcggct gacgag     56

<210> SEQ ID NO 8
<211> LENGTH: 16
<212> TYPE: DNA
<213> ORGANISM: Artificial Sequence
<220> FEATURE:
<223> OTHER INFORMATION: Primer for synthesizing double strand DNA

<400> SEQUENCE: 8
ctcgtcagcc gcctgg                                                16

<210> SEQ ID NO 9
<211> LENGTH: 20
<212> TYPE: DNA
<213> ORGANISM: Artificial Sequence
<220> FEATURE:
```

<223> OTHER INFORMATION: Forward primer for quantitation of AAV titer

<400> SEQUENCE: 9
atcatatgcc aagtacgccc                          20

<210> SEQ ID NO 10
<211> LENGTH: 19
<212> TYPE: DNA
<213> ORGANISM: Artificial Sequence
<220> FEATURE:
<223> OTHER INFORMATION: Reverse primer for quantitation of AAV titer

<400> SEQUENCE: 10
ccaaaaccgc atcaccatg                           19

<210> SEQ ID NO 11
<211> LENGTH: 24
<212> TYPE: DNA
<213> ORGANISM: Artificial Sequence
<220> FEATURE:
<223> OTHER INFORMATION: Forward primer1 for amplification of random
      peptide coding region

<400> SEQUENCE: 11
aaacactcca agtggaacca ccac                     24

<210> SEQ ID NO 12
<211> LENGTH: 22
<212> TYPE: DNA
<213> ORGANISM: Artificial Sequence
<220> FEATURE:
<223> OTHER INFORMATION: Reverse primer1 for amplification of random
      peptide coding region

<400> SEQUENCE: 12
ctgtcccgtg gagtactgtg tg                       22

<210> SEQ ID NO 13
<211> LENGTH: 26
<212> TYPE: DNA
<213> ORGANISM: Artificial Sequence
<220> FEATURE:
<223> OTHER INFORMATION: Forward primer2 for amplification of random
      peptide coding region

<400> SEQUENCE: 13
cagacgaaga ggaaatcagg acaacc                   26

<210> SEQ ID NO 14
<211> LENGTH: 23
<212> TYPE: DNA
<213> ORGANISM: Artificial Sequence
<220> FEATURE:
<223> OTHER INFORMATION: Reverse primer2 for amplification of random
      peptide coding region

<400> SEQUENCE: 14 gccccctgaag gtacacatct ctg                     23

<210> SEQ ID NO 15
<211> LENGTH: 8
<212> TYPE: PRT
<213> ORGANISM: Artificial Sequence
<220> FEATURE:
<223> OTHER INFORMATION: Peptide sequence comprised AAV capsid protein
      mutant

```
<400> SEQUENCE: 15

Val Glu Glu Gly Arg Arg Gly Gln
1               5

<210> SEQ ID NO 16
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 16

Gly Gly Asp Ala Thr Arg Gly
1               5

<210> SEQ ID NO 17
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 17

Gly Gly Gly Arg Val Ala Glu
1               5

<210> SEQ ID NO 18
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 18

Asp Trp Gly Gly Ala Trp Glu
1               5

<210> SEQ ID NO 19
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 19

Gly Gln Ala Gly Gly Ala Ala
1               5

<210> SEQ ID NO 20
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 20

Gly Gly Trp Gly Gly Ser Ala
1               5

<210> SEQ ID NO 21
<211> LENGTH: 7
<212> TYPE: PRT
```

```
<213> ORGANISM: Artificial Sequence
<220> FEATURE:
<223> OTHER INFORMATION: Peptide sequence comprised AAV capsid protein
      mutant

<400> SEQUENCE: 21

Gly Pro Val Asn Gly Gly Gly
1               5

<210> SEQ ID NO 22
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 22

Ala Gly Gly Gly Leu Gly Gly
1               5

<210> SEQ ID NO 23
<211> LENGTH: 6
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 23

Ala Arg Gly Gly Gly Trp
1               5

<210> SEQ ID NO 24
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 24

Gly Ala Met Gly Gly Ser Val
1               5

<210> SEQ ID NO 25
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 25

Ala Val Leu Cys Gly Ala Ala
1               5

<210> SEQ ID NO 26
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 26

Gly Glu Arg Thr Ser Gly Pro
1               5
```

```
<210> SEQ ID NO 27
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 27

Gly Ser Gly Gly Ala Glu Asp
1               5

<210> SEQ ID NO 28
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 28

Gly Val Ala Arg Gly Ala Ala
1               5

<210> SEQ ID NO 29
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 29

Val Gly Gly Ser Leu Val Ser
1               5

<210> SEQ ID NO 30
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 30

Gly Asp Asp Gly Thr Arg Gly
1               5

<210> SEQ ID NO 31
<211> LENGTH: 8
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 31

Val Glu Glu Gly Arg Arg Gly Gln
1               5

<210> SEQ ID NO 32
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant
```

```
<400> SEQUENCE: 32

Val Ala Ser Val Trp Arg Glu
1               5

<210> SEQ ID NO 33
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 33

Gly Thr Ala Ser Ser Gly Gly
1               5

<210> SEQ ID NO 34
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 34

Gly Ala Met Gly Gly Ser Val
1               5

<210> SEQ ID NO 35
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 35

Ala Ser Ala Gly Gly Tyr Gln
1               5

<210> SEQ ID NO 36
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 36

Gly Ala Ser Gly Leu Val Ala
1               5

<210> SEQ ID NO 37
<211> LENGTH: 7
<212> TYPE: PRT
<213> ORGANISM: Artificial Sequence
<220> FEATURE:
<223> OTHER INFORMATION: Peptide sequence comprised AAV capsid protein
      mutant

<400> SEQUENCE: 37

Gly Thr Ala Ser Ser Gly Gly
1               5

<210> SEQ ID NO 38
<211> LENGTH: 20
```

<212> TYPE: DNA
<213> ORGANISM: Artificial Sequence
<220> FEATURE:
<223> OTHER INFORMATION: Forward primer for amplifivation of AsRed2

<400> SEQUENCE: 38
cccaggagat gaagatcgag                                               20

<210> SEQ ID NO 39
<211> LENGTH: 20
<212> TYPE: DNA
<213> ORGANISM: Artificial Sequence
<220> FEATURE:
<223> OTHER INFORMATION: Reverse primer for amplifivation of AsRed2

<400> SEQUENCE: 39
gcttgaagta gtcggggatg                                               20

<210> SEQ ID NO 40
<211> LENGTH: 20
<212> TYPE: DNA
<213> ORGANISM: Artificial Sequence
<220> FEATURE:
<223> OTHER INFORMATION: Forward primer for amplifivation of mouse GAPDH

<400> SEQUENCE: 40
gcaccgtcaa ggctgagaac                                               20

<210> SEQ ID NO 41
<211> LENGTH: 20
<212> TYPE: DNA
<213> ORGANISM: Artificial Sequence
<220> FEATURE:
<223> OTHER INFORMATION: Reverse primer for amplifivation of mouse GAPDH

<400> SEQUENCE: 41
atggtggtga agacgccagt                                               20

<210> SEQ ID NO 42
<211> LENGTH: 45
<212> TYPE: DNA
<213> ORGANISM: Artificial Sequence
<220> FEATURE:
<223> OTHER INFORMATION: mIL12a-fwd primer

<400> SEQUENCE: 42
aacatcgatt gaattcaacg ccgccatgtg tcaatcacgc tacct                   45

<210> SEQ ID NO 43
<211> LENGTH: 35
<212> TYPE: DNA
<213> ORGANISM: Artificial Sequence
<220> FEATURE:
<223> OTHER INFORMATION: mIL12a-rev primer

<400> SEQUENCE: 43
cgactctaga ggatccggcg gagctcagat agccc                              35

<210> SEQ ID NO 44
<211> LENGTH: 97
<212> TYPE: DNA
<213> ORGANISM: Artificial Sequence
<220> FEATURE:
<223> OTHER INFORMATION: mIL12b-fwd primer

<400> SEQUENCE: 44

```
gagctccgcc ggatccgagg gcagaggcag cctgctgacc tgcggcgacg tggaggaaaa      60
ccctggccct agatctatgt gtcctcagaa gctaacc                              97

<210> SEQ ID NO 45
<211> LENGTH: 36
<212> TYPE: DNA
<213> ORGANISM: Artificial Sequence
<220> FEATURE:
<223> OTHER INFORMATION: mIL12b-rev primer

<400> SEQUENCE: 45
tgctcgaggc aagcttctag gatcggaccc tgcagg                               36

<210> SEQ ID NO 46
<211> LENGTH: 6
<212> TYPE: PRT
<213> ORGANISM: Artificial Sequence
<220> FEATURE:
<223> OTHER INFORMATION: Peptide sequence comprising AAV capsid protein
      mutant

<400> SEQUENCE: 46

Gly Asn Arg Gln Ala Ala
1               5

<210> SEQ ID NO 47
<211> LENGTH: 8
<212> TYPE: PRT
<213> ORGANISM: Artificial Sequence
<220> FEATURE:
<223> OTHER INFORMATION: Peptide sequence comrising AAV capsid protein
      mutant

<400> SEQUENCE: 47

Gly Gln Arg Gly Ala Gln Ala Ala
1               5
```